(12) United States Patent
Alsaleh et al.

(10) Patent No.: US 11,714,079 B2
(45) Date of Patent: Aug. 1, 2023

(54) HIGH TEMPERATURE HIGH PRESSURE (HTHP) CELL IN SUM FREQUENCY GENERATION (SFG) SPECTROSCOPY FOR OIL/BRINE INTERFACE ANALYSIS WITH RESERVOIR CONDITIONS AND DYNAMIC COMPOSITIONS

(71) Applicant: SAUDI ARABIAN OIL COMPANY, Dhahran (SA)

(72) Inventors: Salah H. Alsaleh, Dhahran (SA); Dong Kyu Cha, Dhahran (SA); Ali Abdallah Al-Yousef, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/710,374

(22) Filed: Mar. 31, 2022

(65) Prior Publication Data

US 2022/0221440 A1    Jul. 14, 2022

Related U.S. Application Data

(62) Division of application No. 16/787,934, filed on Feb. 11, 2020, now Pat. No. 11,366,091.

(51) Int. Cl.
*G01N 1/10*         (2006.01)
*G01N 1/44*         (2006.01)
(Continued)

(52) U.S. Cl.
CPC .......... *G01N 33/2823* (2013.01); *G01N 1/38* (2013.01); *G01N 1/44* (2013.01); *G01N 21/31* (2013.01);
(Continued)

(58) Field of Classification Search
CPC .. G01N 33/2823; G01N 33/241; G01N 33/24; G01N 15/0826; G01N 15/08;
(Continued)

(56) References Cited

U.S. PATENT DOCUMENTS

2018/0180404 A1* 6/2018 Hunt ...................... G01B 11/24

FOREIGN PATENT DOCUMENTS

| CN | 110132789 A | 8/2019 |
| CN | 111213633 A | 6/2020 |
| JP | 2004111444 A | 4/2004 |

OTHER PUBLICATIONS

Non-Final Office Action issued in related U.S. Appl. No. 16/787,849, dated Jul. 26, 2022 (8 pages).

* cited by examiner

*Primary Examiner* — Andre J Allen
(74) *Attorney, Agent, or Firm* — Osha Bergman Watanabe & Burton LLP

(57) ABSTRACT

A pressure cell for sum frequency generation spectroscopy includes: a metal pressure chamber; a heating stage that heats a liquid sample; an ultrasonic stage that emulsifies the liquid sample; a chamber pump that pressurizes an interior of the metal pressure chamber; and a controller that controls the chamber pump, the ultrasonic stage, and the heating stage to control a pressure of the interior of the metal pressure chamber, an emulsification of the liquid sample, and a temperature of the liquid sample, respectively. The metal pressure chamber includes: a liquid sample holder that retains the liquid sample; a removable lid that seals against a base; a window in the removable lid; a sample inlet that flows the liquid sample from an exterior of the metal pressure chamber to the liquid sample holder at a predetermined flow rate; and a sample outlet.

18 Claims, 7 Drawing Sheets

(51) Int. Cl.
*G02F 1/35* (2006.01)
*E21B 49/00* (2006.01)
*E21B 47/00* (2012.01)
*G01N 33/28* (2006.01)
*G01N 1/38* (2006.01)
*G01N 21/31* (2006.01)
*G05D 16/20* (2006.01)
*G05D 23/19* (2006.01)
*G01K 7/02* (2021.01)
*E21B 47/07* (2012.01)

(52) U.S. Cl.
CPC ......... *G05D 16/2066* (2013.01); *G05D 23/19* (2013.01); *E21B 47/07* (2020.05); *E21B 49/00* (2013.01); *E21B 2200/00* (2020.05); *G01K 7/02* (2013.01); *G01N 2001/386* (2013.01)

(58) Field of Classification Search
CPC ....... G01N 29/024; G01N 2291/02818; G01N 29/07; G01N 11/16; G01N 9/002; G01N 9/26; G01N 33/28; G01N 2291/02836; G01N 2291/044; G01N 29/222; G01N 15/082; G01N 2291/02416; G01N 1/14; G01N 15/088; G01N 33/246; G01N 9/36; G01N 9/24; G01N 29/036; G01N 2291/106; G01N 1/10; G01N 1/2035; G01N 2030/8854; G01N 2291/015; G01N 29/225; G01N 2291/02433; G01N 2291/02854; G01N 24/081; G01N 29/28; G01N 2009/006; G01N 21/31; G01N 21/85; G01N 2291/02872; G01N 2291/105; G01N 29/032; G01N 7/14; G01N 11/08; G01N 11/14; G01N 15/0806; G01N 2291/02827; G01N 27/221; G01N 1/12; G01N 1/2294; G01N 21/8507; G01N 2291/2636; G01N 29/348; G01N 33/383; G01N 11/00; G01N 2291/0421; G01N 2291/102; G01N 29/265; G01N 30/88; G01N 33/18; G01N 1/22; G01N 21/1702; G01N 9/00; G01N 21/274; G01N 2291/014; G01N 2291/048; G01N 29/14; G01N 15/06; G01N 15/0893; G01N 21/552; G01N 7/00; G01N 1/16; G01N 21/3577; G01N 21/359; G01N 2291/011; G01N 25/18; G01N 29/224; G01N 1/08; G01N 2291/02881; G01N 2291/0422; G01N 29/046; G01N 29/38; G01N 13/00; G01N 21/64; G01N 21/65; G01N 2291/2675; G01N 29/069; G01N 3/10; G01N 30/02; G01N 11/04; G01N 2021/1704; G01N 2203/0256; G01N 25/00; G01N 29/02; G01N 29/46; G01N 3/32; G01N 3/58; G01N 33/0006; G01N 33/287; G01N 13/02; G01N 15/04; G01N 2021/1708; G01N 21/3504; G01N 2223/419; G01N 2291/022; G01N 2291/02408; G01N 2291/045; G01N 23/046; G01N 27/223; G01N 29/30; G01N 33/0047; G01N 33/2835; G01N 2001/1025; G01N 2001/2267; G01N 2009/263; G01N 2030/8886; G01N 2291/018; G01N 2291/0427; G01N 25/02; G01N 29/022; G01N 29/11; G01N 29/2425; G01N 1/04; G01N 1/34; G01N 11/167; G01N 2001/2232; G01N 2223/616; G01N 2291/04221; G01N 2291/0256; G01N 2291/101; G01N 25/14; G01N 25/60; G01N 29/028; G01N 29/04; G01N 29/223; G01N 29/2418; G01N 1/2247; G01N 2021/3595; G01N 2021/8528; G01N 2030/025; G01N 2030/146; G01N 21/0303; G01N 21/05; G01N 21/314; G01N 2291/0232; G01N 23/02; G01N 27/02; G01N 27/22; G01N 3/40; G01N 33/225; G01N 15/00; G01N 2001/1031; G01N 2013/0275; G01N 2015/0846; G01N 21/33; G01N 22/00; G01N 22/04; G01N 2291/2634; G01N 23/06; G01N 27/043; G01N 29/245; G01N 29/2462; G01N 29/2468; G01N 3/00; G01N 33/2841; G01N 9/04; G01N 1/18; G01N 1/405; G01N 11/02; G01N 2015/0866; G01N 2021/3129; G01N 2021/855; G01N 21/39; G01N 21/431; G01N 21/5907; G01N 21/94; G01N 21/954; G01N 2201/06113; G01N 2201/0697; G01N 2291/0289; G01N 27/06; G01N 27/74; G01N 29/043; G01N 29/42; G01N 29/4418; G01N 1/2202; G01N 1/24; G01N 1/286; G01N 11/10; G01N 15/0272; G01N 15/0618; G01N 15/0656; G01N 15/0886; G01N 19/04; G01N 2001/1037; G01N 2201/1065; G01N 2001/4016; G01N 2015/0053; G01N 2030/126; G01N 21/255; G01N 21/55; G01N 21/6447; G01N 21/645; G01N 21/718; G01N 21/80; G01N 2203/0053; G01N 2203/0067; G01N 2203/0232; G01N 2203/0676; G01N 2223/635; G01N 2291/0222; G01N 2291/0226; G01N 2291/0231; G01N 2291/024; G01N 2291/103; G01N 23/025; G01N 23/12; G01N 27/82; G01N 27/9046; G01N 29/228; G01N 29/27; G01N 29/32; G01N 3/42; G01N 3/48; G01N 3/56; G01N 30/06; G01N 30/34; G01N 30/8686; G01N 31/10; G01N 31/22; G01N 33/0055; G01N 33/26; G01N 33/2847; G01N 33/42; G01N 5/04; G01N 5/045; G01N 7/04; G01N 7/10; G01N 9/18; G01N 9/28; G01N 9/34; G01N 1/00; G01N 11/06; G01N 11/162; G01N 2001/007; G01N 2001/1427; G01N 2011/0046; G01N 2011/006; G01N 2011/0086; G01N 2013/006; G01N 2015/0833; G01N 2015/084; G01N 2015/1075; G01N 2021/1723; G01N 2021/399; G01N 2021/8557; G01N 2030/143; G01N 2035/0489; G01N 21/00; G01N 21/1717; G01N 21/35; G01N 21/3563; G01N 21/43; G01N 21/534; G01N 21/6402; G01N 21/658; G01N 21/67; G01N 21/69; G01N 21/73; G01N 2291/012; G01N 2291/0224; G01N 2291/0234; G01N 2291/02425; G01N 2291/028; G01N 2291/0426; G01N 23/083; G01N 25/04; G01N 27/07; G01N 27/414; G01N 27/44791; G01N 27/72; G01N 29/22; G01N 29/24; G01N 29/2412; G01N 29/44; G01N 29/4472;

G01N 29/4481; G01N 33/0009; G01N 1/20; G01N 1/2205; G01N 1/2211; G01N 1/2226; G01N 1/26; G01N 1/2813; G01N 1/36; G01N 1/38; G01N 13/04; G01N 15/02; G01N 15/1404; G01N 17/00; G01N 17/02; G01N 19/02; G01N 19/10; G01N 2001/021; G01N 2001/1463; G01N 2001/2007; G01N 2001/2064; G01N 2001/2071; G01N 2001/248; G01N 2001/2866; G01N 2001/2873; G01N 2001/386; G01N 2001/4061; G01N 2001/4066; G01N 2001/4088; G01N 2011/0026; G01N 2011/0053; G01N 2011/0073; G01N 2011/008; G01N 2011/0093; G01N 2011/147; G01N 2013/003; G01N 2013/0266; G01N 2015/0019; G01N 2015/0092; G01N 2015/0096; G01N 2015/0813; G01N 2015/0853; G01N 2015/1413; G01N 2021/0187; G01N 2021/0307; G01N 2021/0346; G01N 2021/1727; G01N 2021/1761; G01N 2021/3174; G01N 2021/3536; G01N 2021/458; G01N 2021/635; G01N 2021/6417; G01N 2021/6421; G01N 2021/6478; G01N 2021/6493; G01N 2021/651; G01N 2021/653; G01N 2021/8405; G01N 2021/8427; G01N 2021/8521; G01N 2030/0095; G01N 2030/047; G01N 2030/567; G01N 2035/00702; G01N 2035/00881; G01N 2035/009; G01N 21/01; G01N 21/11; G01N 21/17; G01N 21/21; G01N 21/211; G01N 21/27; G01N 21/3586; G01N 21/45; G01N 21/51; G01N 21/5911; G01N 21/6452; G01N 21/6486; G01N 21/8806; G01N 21/91; G01N 2201/024; G01N 2201/0696; G01N 2201/084; G01N 2201/12746; G01N 2201/1296; G01N 2203/0005; G01N 2203/0016; G01N 2203/0021; G01N 2203/0023; G01N 2203/0037; G01N 2203/0039; G01N 2203/0044; G01N 2203/005; G01N 2203/0055; G01N 2203/0066; G01N 2203/0073; G01N 2203/0076; G01N 2203/0082; G01N 2203/0083; G01N 2203/0218; G01N 2203/0222; G01N 2203/0226; G01N 2203/023; G01N 2203/024; G01N 2203/0246; G01N 2203/0248; G01N 2203/0266; G01N 2203/0274; G01N 2203/0284; G01N 2203/0286; G01N 2223/076; G01N 2223/423; G01N 2223/649; G01N 2291/01; G01N 2291/021; G01N 2291/0235; G01N 2291/0251; G01N 2291/0258; G01N 2291/02809; G01N 2291/02863; G01N 2291/2626; G01N 2291/267; G01N 2291/269; G01N 2291/2693; G01N 2291/2694; G01N 2291/2698; G01N 23/043; G01N 23/18; G01N 23/201; G01N 23/203; G01N 23/222; G01N 23/223; G01N 25/005; G01N 25/66; G01N 25/72; G01N 27/023; G01N 27/04; G01N 27/12; G01N 27/16; G01N 27/18; G01N 27/185; G01N 27/4035; G01N 27/4146; G01N 27/4168; G01N 27/60; G01N 27/902; G01N 27/9026; G01N 27/9093; G01N 29/045; G01N 29/075; G01N 29/2431; G01N 29/2437; G01N 29/2481; G01N 29/2493; G01N 29/275; G01N 29/40; G01N 29/4436; G01N 29/4445; G01N 29/4454; G01N 29/449; G01N 29/48; G01N 3/064; G01N 3/08; G01N 3/26; G01N 3/307; G01N 3/17; G01N 3/38; G01N 30/28; G01N 30/46; G01N 30/6095; G01N 30/62; G01N 30/8693; G01N 33/0011; G01N 33/0027; G01N 33/0031; G01N 33/0032; G01N 33/0036; G01N 33/004; G01N 33/0057; G01N 33/0075; G01N 33/1866; G01N 33/20; G01N 33/227; G01N 33/2805; G01N 33/2811; G01N 33/2888; G01N 33/30; G01N 33/38; G01N 33/388; G01N 35/00594; G01N 35/00613; G01N 35/00693; G01N 35/1079; G01N 35/1097; G01N 5/00; G01N 5/025; G01N 9/10; G01N 9/266; G01N 9/30; G01N 9/32; G01N 1/2042; G01N 11/165; G01N 15/0205; G01N 15/0255; G01N 15/042; G01N 15/1463; G01N 15/1484; G01N 2001/1056; G01N 2011/0013; G01N 2011/0033; G01N 2015/0011; G01N 2015/0288; G01N 2015/045; G01N 2015/0873; G01N 2021/0375; G01N 2021/0389; G01N 2021/0396; G01N 2021/8592; G01N 2035/00148; G01N 2035/00514; G01N 21/23; G01N 21/59; G01N 21/82; G01N 2201/069; G01N 2201/129; G01N 23/00; G01N 23/16; G01N 24/082; G01N 25/16; G01N 2500/00; G01N 2500/10; G01N 27/08; G01N 27/226; G01N 27/26; G01N 29/00; G01N 29/343; G01N 30/16; G01N 33/1886; G01N 33/5082; G01N 33/5308; G01N 33/574; G01N 33/57411; G01N 33/57415; G01N 33/57419; G01N 33/57423; G01N 33/57434; G01N 33/57484; G01N 33/57488; G01N 33/57492; G01N 35/08; G01N 35/085; E21B 47/06; E21B 47/10; E21B 49/10; E21B 47/00; E21B 49/005; E21B 21/08; E21B 49/008; E21B 49/08; E21B 49/00; E21B 44/00; E21B 49/081; E21B 47/12; E21B 47/01; E21B 47/04; E21B 47/11; E21B 47/09; E21B 49/087; E21B 47/07; E21B 45/00; E21B 49/006; E21B 43/26; E21B 47/017; E21B 47/113; E21B 47/007; E21B 49/022; E21B 49/088; E21B 47/107; E21B 47/18; E21B 47/103; E21B 49/082; E21B 47/024; E21B 49/02; E21B 47/08; E21B 49/003; E21B 33/1243; E21B 47/047; E21B 17/1021; E21B 12/02; E21B 47/117; E21B 49/0875; E21B 47/135; E21B 43/16; E21B 43/12; E21B 47/02; E21B 23/14; E21B 47/002; E21B 33/127; E21B 47/16; E21B 41/00; E21B 47/26; E21B 49/084; E21B 47/13; E21B 17/033; E21B 47/026; E21B 47/085; E21B 43/14; E21B 44/005; E21B 47/009; E21B 21/01; E21B 21/067;

E21B 43/24; E21B 47/005; E21B 49/086;
E21B 17/028; E21B 49/06; E21B 4/02;
E21B 47/14; E21B 41/0085; E21B
33/124; E21B 43/127; E21B 7/04; E21B
47/24; E21B 43/34; E21B 49/083; E21B
23/00; E21B 25/00; E21B 47/003; E21B
23/08; E21B 47/092; E21B 33/138; E21B
43/00; E21B 33/14; E21B 21/001; E21B
33/13; E21B 43/25; E21B 19/08; E21B
19/22; E21B 21/00; E21B 47/001; E21B
7/06; E21B 17/206; E21B 23/04; E21B
25/08; E21B 43/20; E21B 21/06; E21B
33/12; E21B 34/14; E21B 37/06; E21B
47/098; E21B 21/065; E21B 33/1275;
E21B 41/0035; E21B 10/00; E21B
43/121; E21B 21/003; E21B 23/02; E21B
27/02; E21B 43/08; E21B 43/119; E21B
43/122; E21B 17/006; E21B 23/006;
E21B 37/00; E21B 43/38; E21B 47/20;
E21B 17/01; E21B 34/06; E21B 41/02;
E21B 43/267; E21B 7/068; E21B 19/09;
E21B 23/01; E21B 41/0092; E21B 36/04;
E21B 41/0064; E21B 43/11; E21B
47/008; E21B 47/0236; E21B 33/1277;
E21B 21/066; E21B 28/00; E21B 31/03;
E21B 43/128; E21B 19/00; E21B 19/20;
E21B 2200/22; E21B 43/006; E21B
47/053; E21B 47/095; E21B 7/061; E21B
25/005; E21B 33/1208; E21B 34/10;
E21B 43/04; E21B 44/04; E21B 17/10;
E21B 34/066; E21B 43/086; E21B 21/10;
E21B 33/03; E21B 36/003; E21B
43/2401; E21B 49/001; E21B 7/00; E21B
17/1014; E21B 17/16; E21B 17/203;
E21B 21/103; E21B 31/00; E21B
33/0355; E21B 33/06; E21B 34/04; E21B
34/08; E21B 34/16; E21B 41/0021; E21B
43/116; E21B 7/046; E21B 33/064; E21B
33/1246; E21B 33/134; E21B 36/001;
E21B 17/023; E21B 17/1078; E21B
21/062; E21B 29/10; E21B 33/126; E21B
7/067; E21B 17/00; E21B 17/20; E21B
21/085; E21B 23/06; E21B 33/068; E21B
33/1216; E21B 43/003; E21B 43/123;
E21B 43/30; E21B 47/0232; E21B 47/22;
E21B 17/1042; E21B 19/166; E21B
21/16; E21B 25/06; E21B 29/06; E21B
33/043; E21B 33/1294; E21B 36/00;
E21B 41/0057; E21B 43/10; E21B
43/103; E21B 43/117; E21B 43/164;
E21B 43/2406; E21B 19/02; E21B
21/002; E21B 25/02; E21B 3/00; E21B
33/063; E21B 33/085; E21B 34/108;
E21B 34/12; E21B 43/105; E21B
47/0224; E21B 7/12; E21B 7/24; E21B
1/00; E21B 10/32; E21B 10/60; E21B
10/62; E21B 17/025; E21B 17/0283;
E21B 17/042; E21B 17/07; E21B
17/1057; E21B 17/18; E21B 19/16; E21B
19/165; E21B 21/063; E21B 23/10; E21B
25/04; E21B 27/00; E21B 33/072; E21B
33/10; E21B 33/16; E21B 4/00; E21B
43/129; E21B 43/28; E21B 44/02; E21B
47/125; E21B 7/025; E21B 7/062; E21B
7/10; E21B 7/20; E21B 7/28; E21B
17/026; E21B 23/001; E21B 25/16; E21B
31/005; E21B 31/14; E21B 4/18; E21B
41/04; E21B 43/1195; E21B 43/17; E21B
43/305; E21B 7/065; E21B 7/124; E21B
10/02; E21B 10/322; E21B 10/42; E21B
10/64; E21B 17/021; E21B 17/046; E21B
17/08; E21B 17/1035; E21B 19/008;
E21B 19/24; E21B 21/07; E21B 25/10;
E21B 29/00; E21B 29/02; E21B 3/02;
E21B 3/04; E21B 33/04; E21B 33/05;
E21B 33/122; E21B 33/128; E21B
33/1291; E21B 34/02; E21B 34/063;
E21B 35/00; E21B 41/0007; E21B 43/02;
E21B 43/082; E21B 43/114; E21B
43/124; E21B 43/243; E21B 43/40; E21B
44/06; E21B 49/04; E21B 7/022; E21B
7/064; E21B 7/128; E21B 7/26; E21B
10/44; E21B 17/14; E21B 21/12; E21B
2200/05; E21B 31/12; E21B 33/035;
E21B 33/1295; E21B 37/08; E21B 4/04;
E21B 43/281; E21B 43/385; E21B
49/0815; E21B 7/02; E21B 7/265; E21B
1/02; E21B 10/16; E21B 10/20; E21B
10/22; E21B 10/26; E21B 10/46; E21B
10/54; E21B 10/61; E21B 10/66; E21B
12/06; E21B 15/02; E21B 17/015; E21B
17/02; E21B 17/03; E21B 17/04; E21B
17/06; E21B 17/073; E21B 17/1028;
E21B 17/1065; E21B 17/1085; E21B
17/22; E21B 19/002; E21B 19/06; E21B
19/07; E21B 19/083; E21B 19/084; E21B
19/086; E21B 19/089; E21B 19/10; E21B
21/02; E21B 21/106; E21B 21/14; E21B
2200/04; E21B 23/004; E21B 25/18;
E21B 27/005; E21B 29/002; E21B 29/12;
E21B 3/06; E21B 31/06; E21B 31/1075;
E21B 31/16; E21B 31/18; E21B 33/0385;
E21B 33/0407; E21B 33/0415; E21B
33/061; E21B 33/076; E21B 33/1292;
E21B 34/085; E21B 34/101; E21B
34/102; E21B 34/105; E21B 37/10; E21B
4/06; E21B 4/14; E21B 4/145; E21B
4/20; E21B 41/005; E21B 41/0071; E21B
41/0078; E21B 41/0099; E21B 41/08;
E21B 43/017; E21B 43/025; E21B
43/045; E21B 43/084; E21B 43/088;
E21B 43/101; E21B 43/112; E21B
43/1185; E21B 43/162; E21B 43/2408;
E21B 43/255; E21B 43/2607; E21B
43/261; E21B 43/32; E21B 43/36; E21B
44/08; E21B 47/0228; E21B 49/025;
E21B 7/001; E21B 7/021; E21B 7/024;
E21B 7/028; E21B 7/132; E21B 7/14;
E21B 7/18; E21B 7/205; E21B 10/40;
E21B 12/00; E21B 17/0285; E21B
17/085; E21B 23/12; E21B 33/00; E21B
33/0422; E21B 33/129; E21B 34/00;
E21B 37/02; E21B 43/263; E21B 47/013
USPC .............................. 73/152–152.62
See application file for complete search history.

HIGH TEMPERATURE HIGH PRESSURE (HTHP) CELL IN SUM FREQUENCY GENERATION (SFG) SPECTROSCOPY FOR OIL/BRINE INTERFACE ANALYSIS WITH RESERVOIR CONDITIONS AND DYNAMIC COMPOSITIONS

BACKGROUND

Water injection is a common technique used in oil production to increase the yield of hydrocarbons from a reservoir. The interactions between the various phases in the reservoir (e.g., oil, water, brines, calcite rock, and gas) can greatly affect yield of the recovered hydrocarbons. For example, by controlling the salinity and the ionic strength of the injected solution, the wettability of rock formations in the reservoir can be changed to improve recovery. To further improve the yield of hydrocarbons, various spectroscopic techniques such as SFG spectroscopy have been used to understand the nature of the interactions between the phases in the reservoir and characterize the chemical and molecular structure and interfaces of the phases.

SUMMARY

In one aspect, one or more embodiments disclosed herein relate to a pressure cell for SFG spectroscopy. The pressure cell includes a metal pressure chamber that includes a liquid sample holder that retains a liquid sample, a removable lid that seals against a base to enclose the liquid sample holder in an interior of the metal pressure chamber, a window in the removable lid that allows the liquid sample to be optically accessed from an exterior of the metal pressure chamber, a sample inlet that flows the liquid sample from the exterior of the metal pressure chamber to the liquid sample holder in the interior of the metal pressure chamber at a predetermined flow rate, and a sample outlet that flows the liquid sample from the liquid sample holder to the exterior of the metal pressure chamber. The pressure cell further includes: a heating stage, disposed in the interior of the metal pressure chamber, that heats the liquid sample; an ultrasonic stage, disposed in the interior of the metal pressure chamber, that emulsifies the liquid sample; a chamber pump, connected to the interior of the metal pressure chamber, that pressurizes the interior of the metal pressure chamber; and a controller that controls the chamber pump, the ultrasonic stage, and the heating stage to control a pressure of the interior of the metal pressure chamber, an emulsification of the liquid sample, and a temperature of the liquid sample, respectively.

In another aspect, one or more embodiments disclosed herein relate to a system for performing SFG spectroscopy. The system includes: a pressure cell and a sum frequency generation microscope. The pressure cell includes a metal pressure chamber that includes a liquid sample holder that retains a liquid sample, a removable lid that seals against a base to enclose the liquid sample holder in an interior of the metal pressure chamber, a window in the removable lid that allows the liquid sample to be optically accessed from an exterior of the metal pressure chamber, a sample inlet that flows the liquid sample from the exterior of the metal pressure chamber to the liquid sample holder in the interior of the metal pressure chamber at a predetermined flow rate, and a sample outlet that flows the liquid sample from the liquid sample holder to the exterior of the metal pressure chamber. The pressure cell further includes: a heating stage, disposed in the interior of the metal pressure chamber, that heats the liquid sample; an ultrasonic stage, disposed in the interior of the metal pressure chamber, that emulsifies the liquid sample; a chamber pump, connected to the interior of the metal pressure chamber, that pressurizes the interior of the metal pressure chamber; and a controller that controls the chamber pump, the ultrasonic stage, and the heating stage to control a pressure of the interior of the metal pressure chamber, an emulsification of the liquid sample, and a temperature of the liquid sample, respectively. The sum frequency generation microscope includes: a first light source that generates light of a first variable frequency; a second light source that generates light of a second frequency; and a detector that detects light.

In another aspect, one or more embodiments disclosed herein relate to a method of performing SFG spectroscopy. The method includes: sealing a liquid sample holder in an interior of a metal pressure chamber that includes a base and a removable lid; flowing a liquid sample from an exterior of the metal pressure chamber, thorough a sample inlet, to the liquid sample holder in the interior of the metal pressure chamber at a predetermined flow rate; emulsifying the liquid sample with an ultrasonic stage; heating the liquid sample with a heating stage; pressurizing the interior of the metal pressure chamber with a chamber pump that is connected to the interior of the metal pressure chamber; illuminating a surface of the liquid sample with light of a first variable frequency and light of a second frequency through a window of the metal pressure chamber; collecting, through the window, light of a third frequency that is the sum of the first variable frequency and the second frequency from the surface of the liquid sample; and flowing the liquid sample from the liquid sample holder, through a sample outlet, to the exterior of the metal pressure chamber.

Other aspects and advantages will be apparent from the following description and the appended claims.

DETAILED DESCRIPTION

Figure 1A:
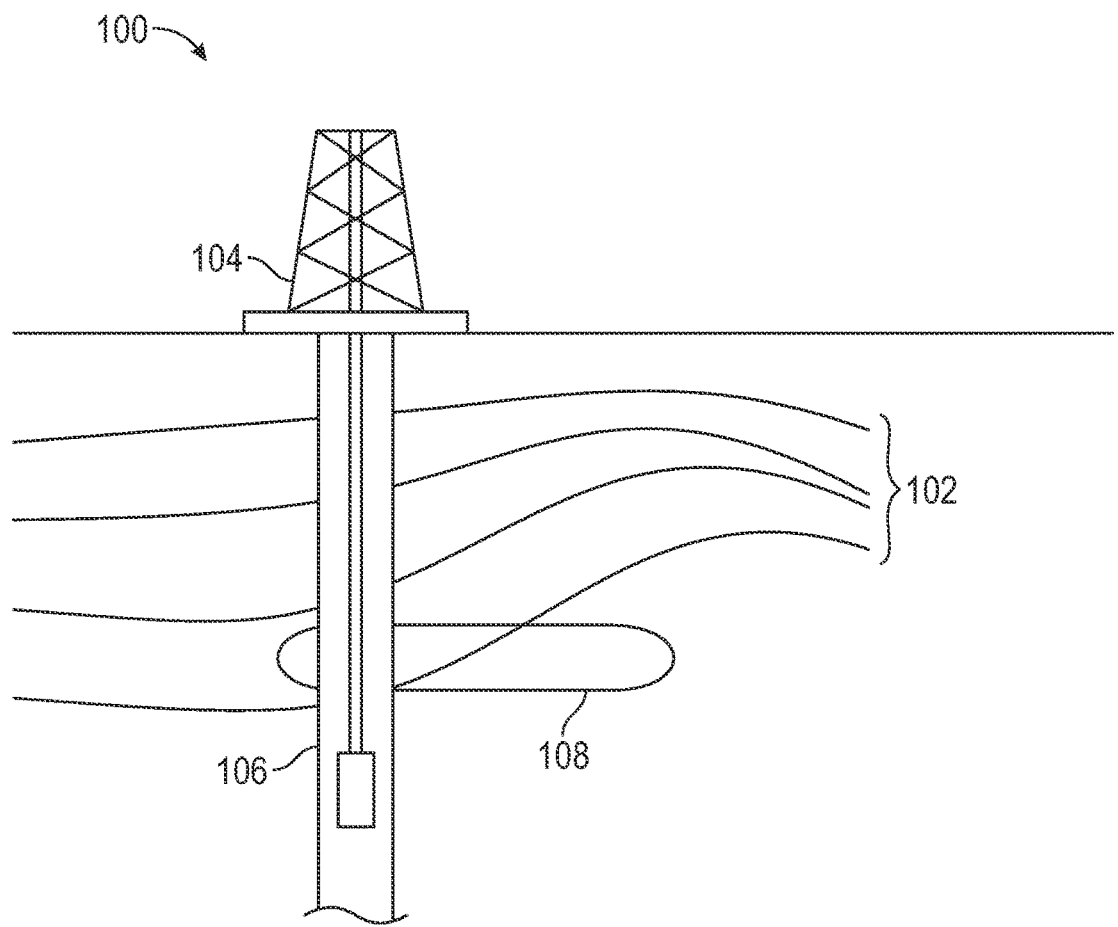
FIG. 1A shows an oil and gas production facility.

Specific embodiments of the present disclosure will now be described in detail with reference to the accompanying figures. Like elements in the various figures are denoted by like reference numerals for consistency.

Numerous specific details are set forth in the following detailed description in order to provide a more thorough understanding of embodiments of the present disclosure. However, it will be apparent to one of ordinary skill in the art that the present disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create a particular ordering of the elements nor to limit any element to being only a single element unless expressly disclosed, such as by the use of the terms "before," "after," "single," and other such terminology. Rather the use of ordinal numbers is to distinguish between the elements. By way of an example, a first element is distinct from a second element, and the first element may encompass more than one element and succeed (or precede) the second element in an ordering of elements.

In general, embodiments disclosed herein provide an apparatus, a system, and a method for performing sum frequency generation (SFG) spectroscopy under simulated reservoir and dynamic conditions to characterize the molecular and chemical structures and interfaces of an oil/brine sample. For example, as shown in FIG. 1, an oil production facility 100 located above a hydrocarbon reservoir 102 may include an oil rig 104 and an oil well 106 to extract hydrocarbons 108. The hydrocarbons 108 may be extracted by pressurizing the reservoir 102 with an injection solution (e.g., conventional water injection, specialized aqueous solution injection) from a second well (not shown).

To improve the effectiveness of the injection recovery technique, the microscopic characteristics of, and interactions between, the hydrocarbons 108, the injection solution, and the rock formations of the reservoir 102 may be studied. Examples of such interactions may include surface charge interaction, ionic exchange, and rock dissolution. SFG spectroscopy may be used to probe the fluid/fluid or fluid/rock interactions and to characterize the chemical and molecular structures and interfaces of a liquid sample, discussed in further detail below. Accordingly, one or more embodiments disclosed herein relate to an apparatus, a system, and a method of studying a liquid sample with SFG spectroscopy in a simulated high temperature and high pressure reservoir environment. Alternatively, other optical techniques (e.g., difference frequency generation (DFG) spectroscopy, Raman spectroscopy) may be used in conjunction with embodiments disclosed herein.

In one or more embodiments, a liquid sample may be extracted from a subsurface facility (e.g., the reservoir 102). For example, a live oil sample may be obtained from the oil well 106. Furthermore, to more closely recreate the actual fluids found downhole in the well (e.g., compositions previously determined using a modular formation dynamic tester (MDT) technique), gases such as gaseous hydrocarbons, hydrogen sulfide, and the like may be remixed into the live oil sample. Alternatively, or in addition, aqueous solutions may be remixed into the live oil sample to recreate the actual fluids found downhole in the well, as described below.

In one or more embodiments, liquid samples collected from the reservoir may be separated into two phases: an organic phase (i.e., primarily hydrocarbons 108 of the live oil sample) and the second component includes an aqueous phase (i.e., primarily water). Then, the two phases may be remixed with a predetermined ratio and/or predetermine level of emulsification. Thus, the liquid sample to be studied may be a synthetic brine (i.e., prepared in a laboratory) comprising the remixed hydrocarbons 108 and an aqueous solution.

The term "brine" is defined as a mixture comprising two or more immiscible liquids. A first component of the brine is dispersed in a second component of the brine. In one or more embodiments, the dispersed first component includes an organic phase (i.e., primarily hydrocarbons) and the second component includes an aqueous phase (i.e., primarily water). Alternatively, the phases of the first and second components may be reversed. In one or more embodiments, the liquid sample may be a brine comprising gaseous hydrocarbons, liquid hydrocarbons, solid hydrocarbons, salts, metals, impurities, water, an aqueous solution, and any combination thereof.

Figure 1B:
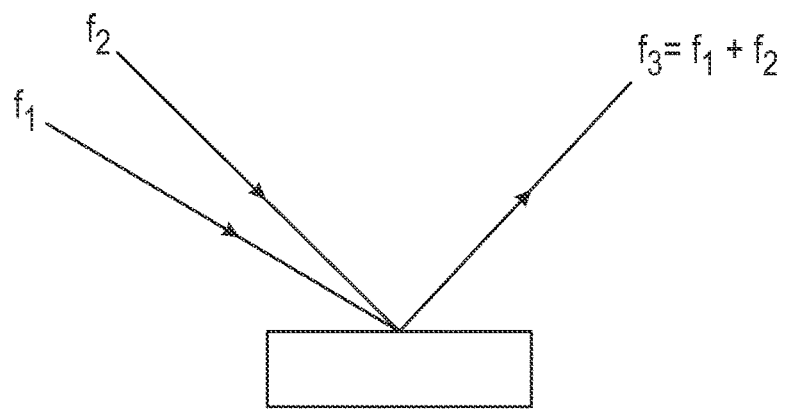
FIG. 1B shows a schematic of a sum frequency generation system.

FIG. 1B shows a schematic of a sum frequency generation system. In sum frequency generation, a sample is probed with two incident light beams that overlap in space (i.e., both beams converge at a coincidence point on the sample) and time (i.e., the pulses from both beams are incident on the sample at the same time). The size of the coincidence point that is probed corresponds to the spot size of the two incident light beams which may be around 150 microns in diameter.

The first light beam is centered at a first variable frequency $f_1$ that may correspond with an energy level of a molecular vibrational mode that occurs in the sample (e.g., corresponds to an infrared wavelength of light). The first variable frequency $f_1$ may be continuously or discretely changed (e.g., with a tunable light source, a filtered light source, a spectrometer, or the like) to probe different energy levels of different molecular vibrational modes in the sample. The first light beam may be incident at an angle of 60° with respect to the normal vector of the sample surface.

The second light beam is centered at a second frequency $f_2$ that is different from the first variable frequency $f_1$ and may correspond to a virtual energy state (e.g., corresponds to a visible wavelength of light). The second light beam may be incident at an angle of 55° with respect to the normal vector of the sample surface. After absorbing the two coincident light pulses, non-linear effects induced by the non-linear susceptibility of the sample causes the surface of the sample to emit light of a third frequency $f_3$ that is the sum of the first and second frequencies $f_1$, $f_2$ (i.e., an SFG signal).

In one or more embodiments, an SFG spectrum is generated by scanning the first variable frequency $f_1$ across a range of frequencies that span an energy level of a molecular vibrational mode of interest. When the first variable frequency $f_1$ corresponds to the energy level of the molecular vibrational mode, the intensity of the emitted SFG light at the third frequency $f_3$ will increase due to a resonant effect of the first light beam exciting the molecular vibrational mode. By analyzing the intensity of the detected third frequency of light $f_3$, the vibrational modes in the sample may be identified from the resonant frequencies. Furthermore, the directional dependence of the non-linear susceptibility of the sample allows a user to derive information about the orientation of molecules in the sample from the polarization of the collected SFG signal.

In one or more embodiments, the first light beam may be a spectrally broadband light beam that includes a plurality of frequencies $f_1$ while the second light beam remains at a single fixed frequency $f_2$. Accordingly, the emitted SFG light from the sample would include a plurality of third frequencies $f_3$ that may be collected simultaneously for faster data acquisition.

Figure 2:
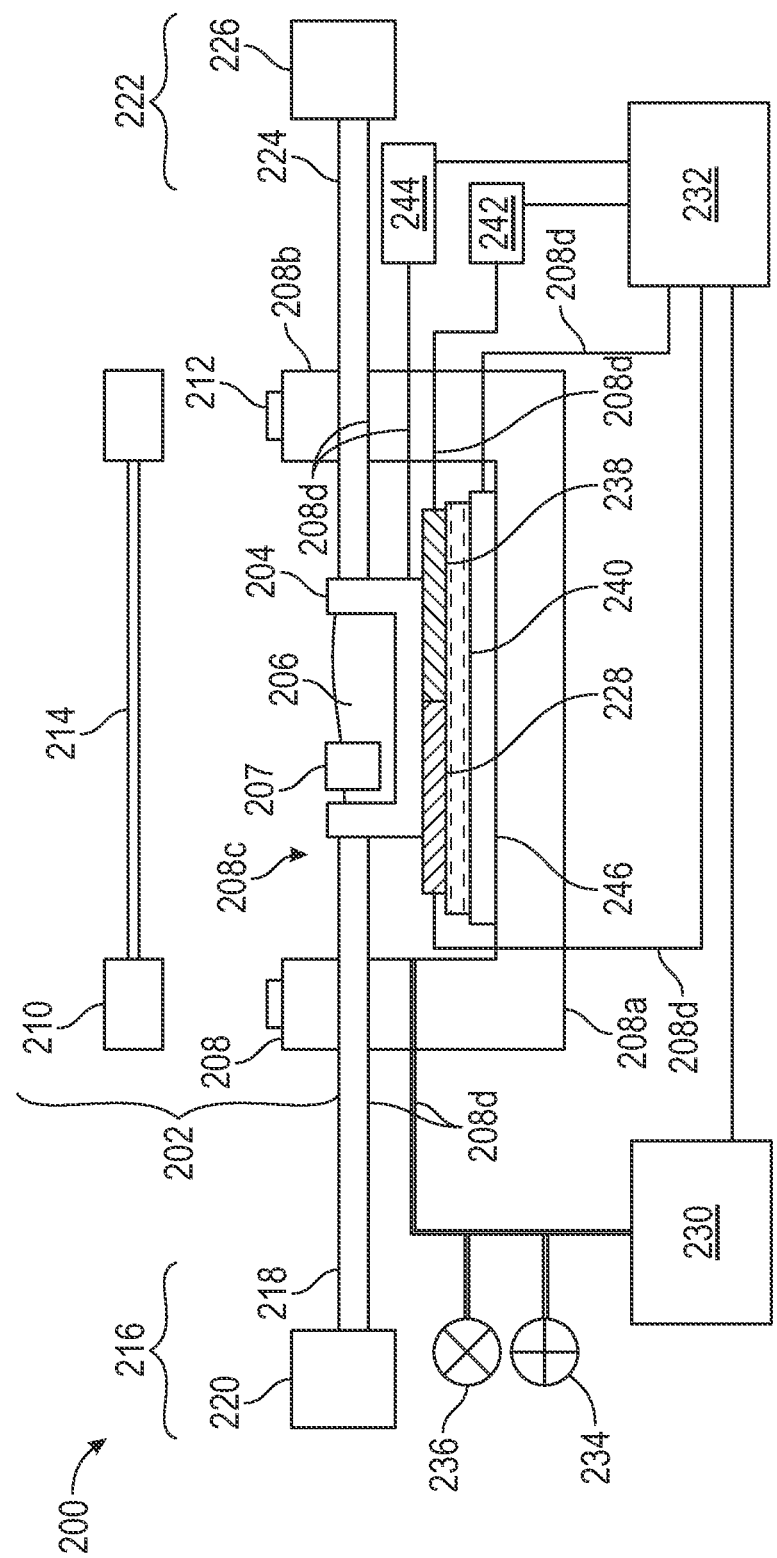
FIG. 2 shows an open pressure cell for SFG spectroscopy according to one or more embodiments.
Figure 3:
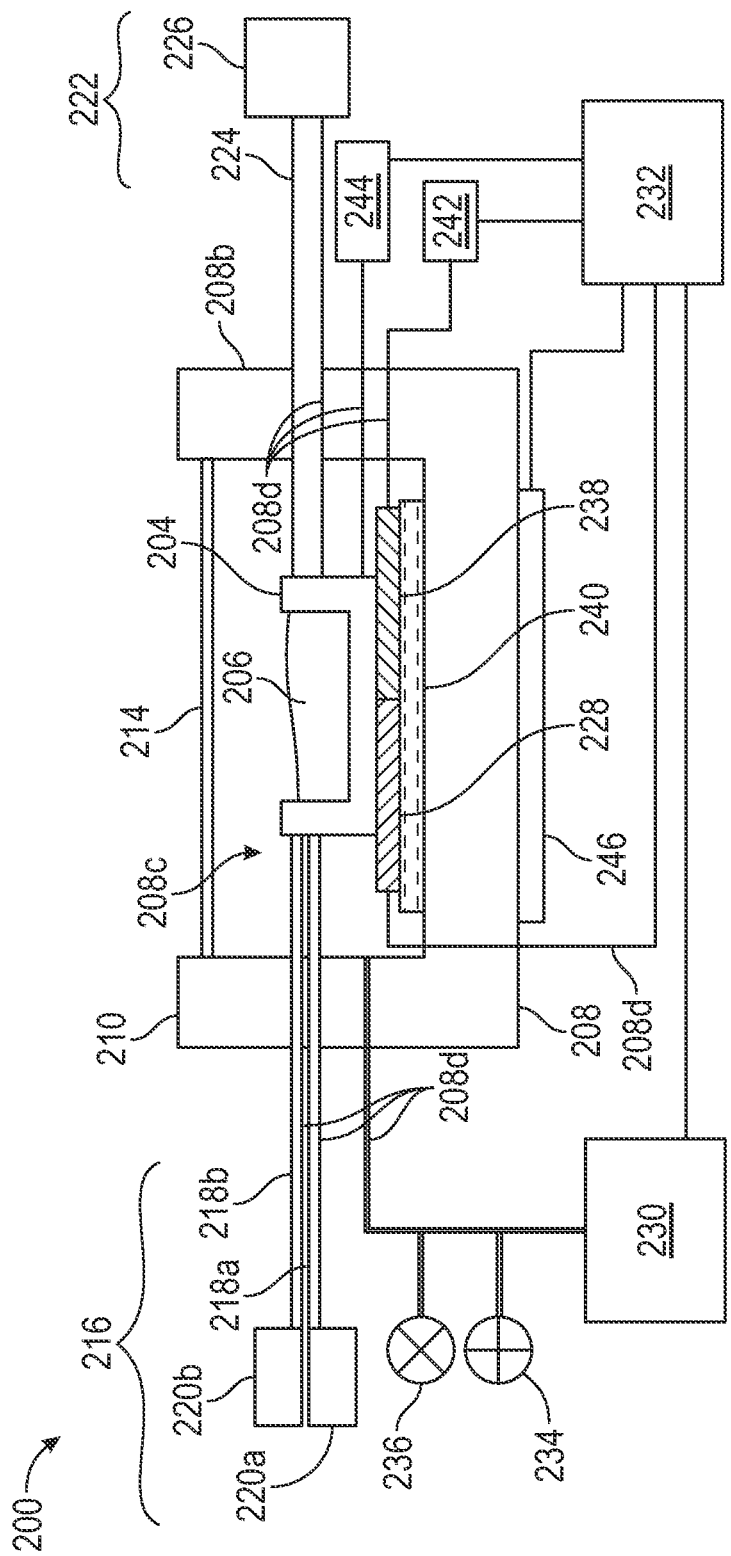
FIG. 3 shows a sealed pressure cell for SFG spectroscopy according to one or more embodiments.

FIGS. 2 and 3 show a pressure cell 200 for SFG spectroscopy according different embodiments of the present invention. The pressure cell 200 simulates conditions that occur in the reservoir 102 (FIG. 1). The pressure cell 200 includes a metal pressure chamber 202 that encloses a liquid sample holder 204 that retains a liquid sample 206 (e.g., a brine). In one or more embodiments, the liquid sample holder 204 may include a rock interface 207 (e.g., a calcite rock sample, a dolomite rock sample, an anhydrite mineral sample, a part of a carbonite rock sample, or any combination thereof) or any other appropriate material to interact with the liquid sample 206 to further simulate interactions that occur in the reservoir 102 (FIG. 1).

The metal pressure chamber 202 includes a base 208 and a removable lid that enclose the liquid sample holder 204 within the metal pressure chamber 202. The base 208 and the removable lid 210 are formed from a metal and may be aluminum, stainless steel, or any other appropriate metal with sufficient strength to withstand the temperatures and pressures of a simulated reservoir environment. In one or more embodiments, the metal pressure chamber 202 may have a circular cross-section and a diameter of at least 20 cm. Alternatively, the metal pressure chamber may have a rectangular cross-section. However, the metal pressure chamber 202 is not limited to these shapes or dimensions and any appropriate size or shape may be used.

As shown in FIG. 2, in one or more embodiments, the base 208 may comprise a horizontal base plate 208a and a vertical wall(s) 208b that extends in a direction perpendicular to the base plate 208a. The base plate 208a and wall(s) 208b define a cavity 208c that retains the liquid sample holder 204. The base 208 includes an interior surface that is exposed to the simulated environment created in an interior of the metal pressure chamber 202 and an exterior surface that is exposed to an external environment of the metal pressure chamber 202. In one or more embodiments, the base 208 may further include one or more feedthroughs 208d that communicate between the interior surface and the exterior surface of the base 208.

A feedthrough 208d may be a channel, a port, a fluid path, a length of tubing, an electrical line, an electrical conduit, an electrical plug, or any combination thereof depending on the material or signal being passed through the base 208. For example, one or more feedthroughs 208d may be electrical conduits that pass signals (e.g., control signals) or power to equipment inside the metal pressure chamber 202, as described below. In addition, one or more feedthroughs 208d may include a channel connected to a chamber pump 230, described below, that pressurizes the interior of the metal pressure chamber 202. Further still, one or more feedthroughs 208d may include various tubes that introduce and remove the liquids sample 206 to and from the interior of the metal pressure chamber 202.

As discussed above, the removable lid 210 cooperates with the base 208 to form the metal pressure chamber 202 that encloses the liquid sample holder 204. The removable lid 210 may be a planar plate that seals against an upper surface of the wall(s) 208b of the base 208. The removable lid 210 may attach to the base 208 by a set of cooperating threads (i.e., screws onto the base 208), one or more clips (i.e., clipped onto the base 208), or by fastening one or more fasteners (e.g., bolts, screws). However, the removable lid 210 may attach to the base 208 by any appropriate means that provides a seal to contain the pressure of the simulated reservoir environment. As shown in FIG. 2, in one or more embodiments, a seal 212 may be disposed between the base 208 and the removable lid 210 to isolate the simulated environment inside the metal pressure chamber 202 from the external environment of the metal pressure chamber 202. The seal 212 may be an elastomer O-ring, a copper gasket, any other appropriate sealing material, or any combination thereof.

In one or more embodiments, the removable lid 210 comprises a window 214 that allows the liquid sample 206 to be optically accessed from the exterior of the metal pressure chamber 202 (e.g., to allow light from an external source to access the liquid sample 206). The window 214 may be transparent to a first, a second, and a third frequency of light (i.e., frequencies $f_1$, $f_2$, and $f_3$), where the third frequency $f_3$ is the sum of the first and second frequencies $f_1$, $f_2$. The window 214 may be made of glass (e.g., a silica based glass, a calcium fluoride based glass, or the like) that is transparent enough to allow the liquid sample 206 to be illuminated with light of the first and second frequencies $f_1$, $f_2$ from a source disposed outside of the metal pressure chamber 202. The window 214 may also be transparent enough to pass the generated SFG signal comprising light of the third frequency $f_3$ from the liquid sample 206 to a detector disposed outside of the metal pressure chamber 202. The window 214 may have a refractive index of approximately 1.5. The window 214 may be coated with an antireflection coating.

In one or more embodiments, the window 214 may comprise multiple transparent windows. For example, the removable lid 210 may comprise three distinct windows 214, wherein the optical properties (e.g., transmission coefficient) of each window 214 is tuned to a corresponding first, second, and third frequency $f_1$, $f_2$, $f_3$ of light, respectively.

In general, the base 208 and the removable lid 210 cooperate to enclose the liquid sample holder 204 and the window 214 allows external light to access the liquid sample 206. However, other embodiments may be devised without departing from the scope of embodiments disclosed herein. For example, the base 208 may comprise only a base plate 208a while the wall(s) that define the cavity 208c of the metal pressure chamber 202 may be disposed on the removable lid 210. In this configuration, the base 208 may be removable from the lid 210. Accordingly, the one or more feedthroughs 208d may be disposed on the lid 210 rather than the base 208.

As discussed above, the metal pressure chamber 202 encloses a liquid sample holder 204 that retains the liquid sample 206. The liquid sample holder 204 may be made of any appropriate material that retains the liquid sample 206. In one or more embodiments, the liquid sample holder 204 is made of a non-corrosive material (e.g., a stainless steel, a polymer, TEFLON, or the like) that can be easily cleaned of the liquid sample 206 and reused. For example, the liquid sample holder 204 may be made of TEFLON which exhibits excellent chemical and temperature resistance up to 250° C.

The liquid sample holder 204 may be any shape (e.g., circular cross-section, non-circular cross-section) provided that the liquid sample 206 retained by the liquid sample holder 204 is exposed to the interior of the metal pressure chamber 202. In one or more embodiments, the liquid sample holder 204 may be an open cylinder with a circular cross-section and a diameter of 10-15 cm. The liquid sample holder 204 may retain 15-20 mL of the liquid sample 206. However, any appropriate size or shape may be used to retain the liquid sample 206 provided the liquid sample holder 204 fits within the metal pressure chamber 202.

In one or more embodiments, the metal pressure chamber 202 further includes a sample inlet 216 that flows the liquid sample 206 from the exterior of the metal pressure chamber 202 to the liquid sample holder 204 in the interior of the metal pressure chamber 202. The sample inlet 216 may include a sample inlet path 218 connected to the liquid sample holder 204 and a sample pump 220 that pumps the liquid sample 206 through the sample inlet path 218 and into the liquid sample holder 204.

The sample inlet path 218 may be a rigid or flexible tubing that passes through the base 208 via a feedthrough 208d and directly connects to the liquid sample holder 204. The sample inlet path 218 may be disposed to flow the liquid sample 206 directly into the liquid sample holder 204 (e.g., one end of the sample inlet path is directly connected to a wall of the liquid sample holder). In one or more embodiments, the sample inlet path 218 is disposed to flow the liquid sample 206 onto the rock interface 207 disposed in the liquid sample holder 204.

The sample pump 220 may be a metering pump that generates a predetermined flow rate of the liquid sample 206 in the sample inlet path 218. For example, the sample pump 220 may generate a maximum inlet flow rate of 50 mL/min and a minimum inlet flow rate of 0.001 mL/min. However, depending on the reservoir conditions that are being simulated, other flow rates may be used. The sample pump 220 may be a Quizix Q6000 high pressure syringe pump (Chandler Engineering). In one or more embodiments, the sample pump 220 may include a sample storage container or a sample preparation device (e.g., a mixer that combines an organic phase and an aqueous phase to create the liquid sample 206).

In one or more embodiments, the sample inlet 216 may further comprise an inlet valve that seals the sample inlet path 218. The inlet valve may completely seal the sample inlet path 218 to prevent the pressurized environment in the interior of the metal pressure chamber 202 from forcing the liquid sample 206 back into the sample pump 220. Alternatively, the inlet valve may be controlled to partially seal the sample inlet path 218 to regulate the flow rate of the liquid sample 206 from the sample pump 220.

As shown in FIG. 3, in one or more embodiments where the liquid sample 206 is a brine, the sample inlet 216 may include a plurality of sample inlet paths 218a, 218b, each with a corresponding sample pump 220a, 220b that pumps a portion of the liquid sample 206 into the liquid sample holder 204. For example, a first sample inlet path 218a may flow an aqueous phase of the liquid sample 206 into the liquid sample holder 204 at a first partial flow rate. A second sample inlet path 218b may flow an organic phase of the liquid sample 206 into the liquid sample holder 204 at a second partial flow rate. In other words, the liquid sample 206 may be a brine that is mixed inside of the pressure cell 200. As discussed in further detail below, an ultrasonic stage 228 may prepare the liquid sample 206 for study by emulsifying (i.e., mixing) the organic and aqueous phases to more accurately recreate sample compositions and liquid/liquid or liquid/solid interfaces found in the reservoir 102 (FIG. 1).

The metal pressure chamber 202 further includes a sample outlet 222 that flows the liquid sample 206 from the liquid sample holder 204 in the interior of the metal pressure chamber 202 to the exterior of the metal pressure chamber 202. The sample outlet 222 may include a sample outlet path 224 connected to the liquid sample holder 204 and a sample drain 226 that removes the liquid sample 206 from the metal pressure chamber 202.

The sample outlet path 224 may be a rigid or flexible tubing that passes through the base 208 via a feedthrough 208d and directly connects to the liquid sample holder 204. In one or more embodiments, the sample outlet path 218 may the same type of tubing as the sample inlet path 218.

The sample drain 226 may be a sample storage container or a sample disposal container. In one or more embodiments, the flow in the sample outlet path 224 and out of the sample drain 226 may be passively generated by the sample pump 220 introducing a new portion of the liquid sample 206 into the liquid sample holder 204. Alternatively, the sample drain 226 may also include a pump (e.g., a syringe pump) to actively extract the liquid sample 206 from the metal pressure chamber 202.

In one or more embodiments, the sample drain 226 may further comprise an outlet valve that seals the sample outlet path 224. The outlet valve may completely seal the sample outlet path 224 to prevent the pressurized environment in the interior of the metal pressure chamber 202 from forcing the liquid sample 206 out of the pressure cell. Alternatively, the outlet valve may be controlled to partially seal the sample outlet path 224 to regulate the flow of the liquid sample 206 through the sample drain 226.

The combination of the sample inlet 216 and the sample outlet 222 allows the composition of the liquid sample 206 in the metal pressure chamber 202 to be changed in situ. In other words, the composition of the liquid sample 206 and the liquid/liquid or liquid/solid interfaces found in the liquid sample holder 204 may be actively changed and manipulated to simulate dynamic conditions of the reservoir 102. For example, the liquid sample 206 may be diluted by introducing an aqueous injection solution via the sample inlet 216 to simulate the displacement of an oil/brine sample by conventional water injection recovery techniques.

The pressure cell 200 further includes an ultrasonic stage 228 that is directly connected to the liquid sample holder 204. The ultrasonic stage 228 may be a vibrating table, a vibrating probe, an ultrasonic bath, or any other appropriate mechanism that sonicates the liquid sample 206 in the liquid sample holder 204. In one or more embodiments, the ultrasonic stage 228 may be vibrationally isolated from the metal pressure chamber 202 (e.g., to prevent misalignment of the incident light beams at the surface of the liquid sample 206 or to prevent loosening of the sealed connection between the base 208 and removable lid 210). For example, a thermal isolation layer 240, discussed in further detail below, may absorb mechanical vibrations from the ultrasonic stage 228.

The ultrasonic stage 228 may be connected to a controller 232 that provides power and control signals to the ultrasonic stage 228. The controller 232, described in further detail below with respect to FIG. 4, may control the ultrasonic stage 228 based information from the sample inlet 216 and sample outlet 222. For example, the controller 232 may control the ultrasonic stage 228 to emulsify the liquid sample 206 only when the sample inlet 216 and sample outlet 222 have completed setting or altering of the composition of the liquid sample 206. In one or more embodiments, the ultrasonic stage 228 may emulsify an aqueous phase and an organic phase of the liquid sample 206 for 30 seconds to generate a brine, an oil/water emulsion, or a nano-sized oil emulsion.

The pressure cell 200 further includes a chamber pump 230 that is connected to, and pressurizes, the interior of the metal pressure chamber 202. The chamber pump 230 may be a vacuum pump, a compressor, a pneumatic compressor, a hydraulic compressor, any other appropriate mechanism that generates a pressurized environment in the interior of the metal pressure chamber 202, or any combination thereof. In one or more embodiments, the chamber pump 230 may be vibrationally isolated from the metal pressure chamber 202 (e.g., to prevent misalignment of the incident light beams at the surface of the liquid sample 206 or to prevent loosening of the sealed connection between the base 208 and removable lid 210). For example, the feedthrough 208d and/or the tubing that connects the chamber pump 230 and the metal pressure chamber 202 may absorb mechanical vibrations from the chamber pump 230.

The pressure range of the chamber pump 230 may be between ambient atmospheric pressure (e.g., around 14.7 psi) to approximately 3000 psi. However, as conditions in a reservoir 102 (FIG. 1) may vary according to many parameters (e.g., depth, geographic location, rock composition), the pressure range of the chamber pump 230 is not limited to this approximate value and pressures greater than 3000 psi may be implemented. In one or more embodiments, the chamber pump 230 may further comprise a vacuum pump that evacuates the metal pressure chamber 202 (e.g., to outgas components).

The chamber pump 230 may be connected to a controller 232 that provides power and control signals to the chamber pump 230. The controller 232, described in further detail below with respect to FIG. 4, may control the chamber pump 230 based upon a pressure gauge 234 that measures a pressure of the interior of the metal pressure chamber 202. Furthermore, the controller 232 may also control a control valve 236 that seals the metal pressure chamber 202 from the chamber pump 230. Furthermore, the controller 232 may open the control valve 236 to release pressure from the interior of the metal pressure chamber 202. In other words, the controller 232 may control the chamber pump 230 and the control valve 236 to control (e.g., increase, decrease, maintain) the pressure in the metal pressure chamber 202.

The pressure cell 200 further includes a heating stage 238 (e.g., a heating element) that heats the liquid sample 206. In one or more embodiments, the heating stage 238 is an electric heater (e.g., electrical joule heater, ohmic heater), however any appropriate heating element may be used to heat the liquid sample 206. The heating stage 238 may be directly connected to the liquid sample holder 204. In some embodiments, a thermal isolation layer 240 may be disposed on the heating stage 238 (e.g., between the heating stage 238 and the metal pressure chamber 202) to thermally isolate the heating stage 238 from the metal pressure chamber (i.e., prevent the metal pressure chamber 202 from unnecessarily heating during operation). The thermal isolation layer 240 may be made of mica. Alternatively, the thermal insulation layer may a ceramic that includes one or more of aluminum oxide ($Al_2O_3$), silica ($SiO_2$), magnesium oxide (MgO), or any combination thereof.

The temperature range of the heating stage 238 may be between 25-100 C.° to simulate the temperatures of the reservoir 102. However, as conditions in a reservoir 102 (FIG. 1) may vary according to many parameters (e.g., depth, geographic location, rock composition), the temperature range of the heating stage 238 is not limited to this range and temperatures greater than 100 C.° may be implemented.

The heating stage 238 may be connected to a temperature controller 242 disposed outside of the metal pressure chamber 202. The temperature controller 242 may be a hardware or software component of the controller 232 or may be a distinct controller apparatus. The temperature controller 242 provides power and control signals to the heating stage 238 through one or more feedthroughs 208d in the metal pressure chamber 202. The temperature controller 242 may control the heating stage 238 based on a temperature of the liquid sample 206 that is measured by a thermocouple 244 connected to the liquid sample holder 204.

In one or more embodiments, the pressure cell 200 further includes a positioning stage 246 that controls a position of a surface of the liquid sample 206. The positioning stage 246 may include one or more actuators (e.g., an electric actuator, a pneumatic actuator, a hydraulic actuator, a piezoelectric actuator, or any combination thereof) that translates the base 208 or the liquid sample holder 204 in one or more dimensions (e.g., a vertical direction) to align the surface of the liquid sample 206 with the incident light beams. The positioning stage 246 may automatically position the surface of the liquid sample 206 based on optical feedback from the surface of the liquid sample 206, as described in further detail below with respect to FIG. 5. The positioning stage 246 may be controlled by the controller 232.

In one or more embodiments, the positioning stage 246 may be disposed on an interior surface of base 208, as shown in FIG. 2. The positioning stage 246 may translate the liquid sample holder 204, the heating stage 238, and the ultrasonic stage 228 to align the surface of the liquid sample with respect to the incident light. The positioning stage 246 may be separated from the heating stage 238 by the thermal insulation layer 224 that prevents the positioning stage 246 from unnecessarily heating up during operation.

In another embodiment, as shown in FIG. 3, the positioning stage 246 may be disposed exteriorly to the metal pressure chamber 202 while the heating stage 238 is disposed in the interior of the metal pressure chamber 202. The positioning stage 246 may translate the metal pressure chamber 202 and the entire contents thereof to align the surface of the liquid sample 206 with respect to the incident light. An external positioning stage 246 advantageously reduces the number of feedthroughs 208d and the possibility of leaks from the metal pressure chamber 202.

Figure 4:
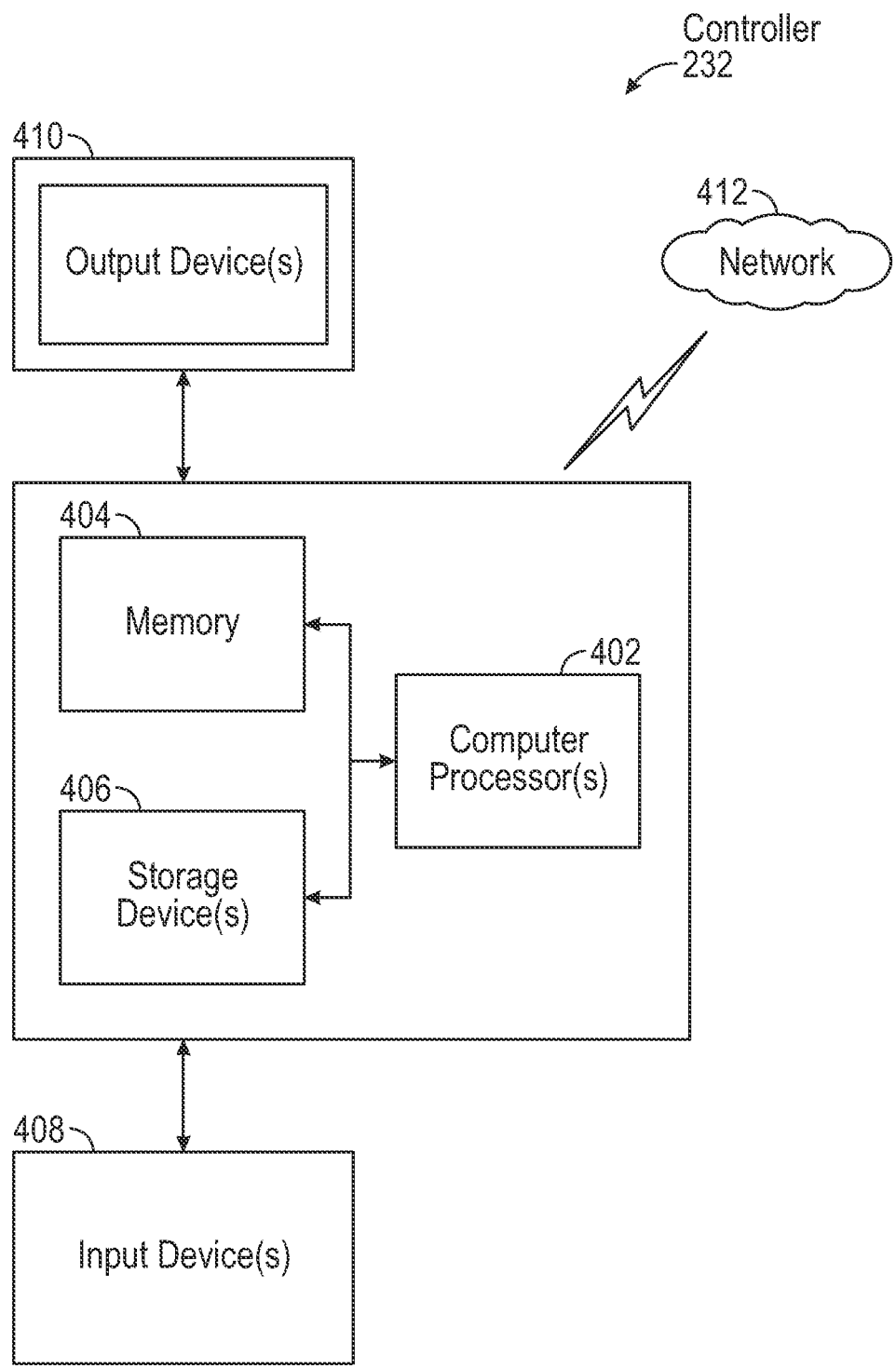
FIG. 4 shows a schematic of a controller according to one or more embodiments.

FIG. 4 shows a schematic of a controller 232 according to one or more embodiments. As discussed above, in one or more embodiments, the controller 232 may control the chamber pump 230, the heating stage 238, and the ultrasonic stage 228 to control a pressure of the interior of the metal pressure chamber 202, a temperature of the liquid sample 206, and an emulsification of the liquid sample 206, respectively. The controller 232 may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments disclosed herein. For example, as shown in FIG. 4 the controller 232 may include one or more computer processor(s) 402, associated memory 404 (e.g., random access memory (RAM), cache memory, flash memory), one or more storage device(s) 406 (e.g., a hard disk, an optical drive such as a compact disk (CD) drive or digital versatile disk (DVD) drive, a flash memory stick), and numerous other elements and functionalities. The computer processor(s) 402 may be an integrated circuit for processing instructions. For example, the computer processor(s) may be one or more cores, or micro-cores of a processor.

The controller 232 may also include one or more input device(s) 408, such as a pressure gauge 234, thermocouple 244, SFG microscope 500 (discussed in further detail with respect to FIG. 5), camera, imager, touchscreen, keyboard, mouse, microphone, touchpad, electronic pen, or any other type of input device. Further, the controller 232 may include one or more output device(s) 410, such as a screen (e.g., a liquid crystal display (LCD), a plasma display, touchscreen, cathode ray tube (CRT) monitor, or other display device), a printer, external storage, or any other output device. One or more of the output device(s) may be the same or different from the input device(s). The controller 232 may be connected to a network 412 (e.g., a local area network (LAN), a wide area network (WAN) such as the Internet, mobile network, or any other type of network) via a network interface connection (not shown). The input and output device(s) may be locally or remotely (e.g., via the network 412) connected to the computer processor(s) 402, memory 404, and storage device(s) 406. Many different types of computing systems exist, and the aforementioned input and output device(s) 408, 410 may take other forms.

Further, one or more elements of the controller 232 may be located at a remote location and be connected to the other elements over a network 412. Further, one or more embodiments may be implemented on a distributed system having a plurality of nodes, where each portion of the embodiment may be located on a different node within the distributed system. In one embodiment, the node corresponds to a distinct computing device. In other embodiments, the node may correspond to a computer processor with associated physical memory. In yet other embodiments, the node may correspond to a computer processor or micro-core of a computer processor with shared memory and/or resources.

Figure 5:
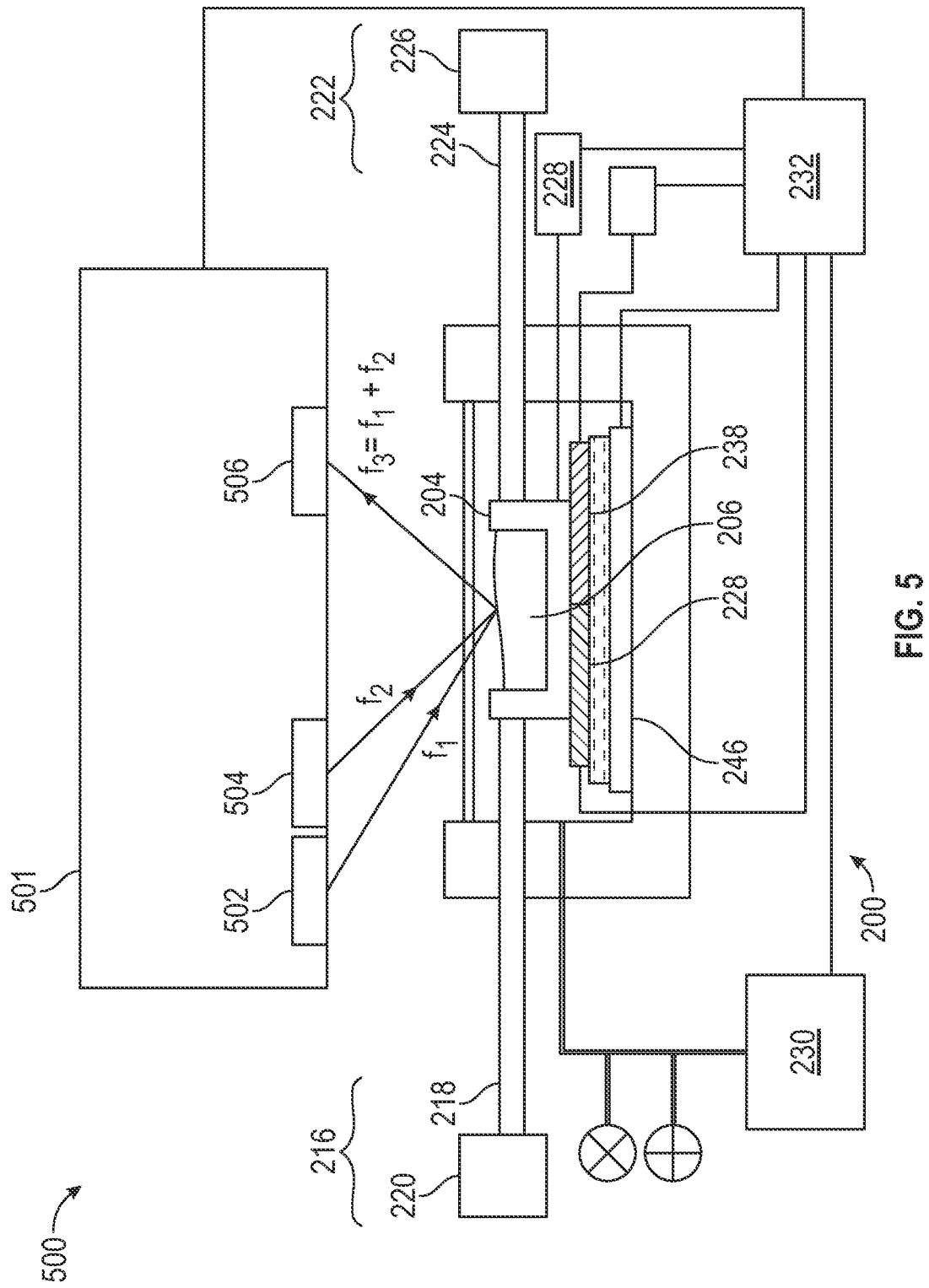
FIG. 5 shows a system for performing SFG spectroscopy according to one or more embodiments.

FIG. 5 shows a system 500 for performing SFG spectroscopy according to one or more embodiments. A system 500 for performing SFG spectroscopy may include a pressure cell 200, as previously described with respect to the embodiments of FIGS. 2-3, and an SFG microscope 501. The SFG microscope 501 may be an SFG vibrational spectrometer (Ekspla), for example.

The SFG microscope 501 includes a first light source 502 that generates light of the first variable frequency $f_1$. The range of the first variable frequency $f_1$ may correspond to the vibrational energy of a molecule in the liquid sample (e.g., corresponds to an infrared wavelength of light). The first light source 502 may be disposed to focus the light of the first variable frequency $f_1$ on the surface of the liquid sample 206 with an incidence angle of 60° with respect to a surface normal vector. In one or more embodiments, the first light source 502 is pulsed laser source with a pulse energy of 2.7-35 mJ and a pulse duration of 28+/−10 picoseconds. For example, the first light source 502 may comprise a PL2231-50 picosecond laser centered at 1064 nm (Ekspla) that feeds into a SFGH500 multichannel beam delivery unit (Ekspla) that feeds a PG501-DFGx optical parametric generator (Ekspla) that outputs a variable IR wavelength ranging of 2300-16000 nm. The first light source may further include a visible laser to aid in focusing the light of the variable frequency $f_1$.

The SFG microscope 501 further includes a second light source 504 that generates light of the second frequency $f_2$. The second frequency $f_2$ is different from the first variable frequency $f_1$ and may correspond to a virtual energy state (e.g., may correspond to a visible wavelength of light). The second light source 504 may be disposed to focus the light of the second frequency $f_2$ on the surface of the liquid sample 206 with an incidence angle of 55° with respect to a surface normal vector. In one or more embodiments, the second light source 504 is pulsed laser source with a pulse energy of 2.7-35 mJ and a pulse duration of 28+/−10 picoseconds. For example, the second light source 502 may be a second output of the PG501-DFGx optical parametric generator (Ekspla) that outputs a fixed 532 nm wavelength.

However, the present disclosure is not limited to this configuration and any appropriate light sources for generating an SFG signal (i.e., light of the third frequency $f_3$ that is the sum of the first and second frequencies $f_1$, $f_2$) may be used. The first and second light sources 502, 504 are configured to spatially and temporally overlap the first and second light beams at the surface of the liquid sample 206 to generate the SFG signal. The SFG signal may be a pulsed signal with a pulse energy of 0.52-5.3 mJ and a pulse duration of 28+/−10 picoseconds.

The SFG microscope 501 further comprises a detector 506 that detects light. The detector 506 is offset from the light sources 502, 504 of the SFG microscope 501 to collect the SFG signal emitted from the liquid sample 206. The detector 506 may include additional optical elements (e.g., lens, spatial filter, frequency filter, spectrometer, power meter) to control, measure, and manipulate the detected light. For example, in one or more embodiments where multiple vibrational frequencies are probed simultaneously, the detector 506 may be a monochromator that collects and spectrally separates different frequencies of light in the collected signal.

In one or more embodiments, the SFG microscope 501 may further include additional optical elements (e.g., mirror, lens, spatial filter, frequency filter, delay line, spectrometer, power meter) to control, measure, and manipulate the emitted and detected light.

In one or more embodiments, the SFG microscope 501 may be controlled by the controller 232. For example, the controller 232 may instruct the SFG microscope 501 to begin data acquisition once the chamber pump 230 has pressurized the metal pressure chamber 202 to a predetermined pressure, the heating stage 238 has heated the liquid sample 206 to a predetermined temperature measured by the thermocouple 228, and the ultrasonic stage 228 has emulsified the liquid sample 206 to a predetermined degree of emulsification.

In one or more embodiments, the controller 232 may halt data acquisition while the sample inlet 216 and sample outlet 222 control the composition of the liquid sample 206 in the liquid sample holder 204. Specifically, adjusting the flow rate of the liquid sample 206 or adding/removing a quantity of the liquid sample 206 may modify the position of the surface of the liquid sample 206 and disrupt the spatial overlap of the first and second light beams at the surface. Furthermore, the controller 232 may halt data acquisition while the liquid sample 206 is being emulsified because the surface of the liquid sample 206, and thus the spatial overlap of the first and second light beams, may be disrupted by the ultrasonic stage 228 process.

Furthermore, the controller 232 may use one or more of the first and second light sources 502, 504 to illuminate the liquid sample 206 to align the liquid sample holder 204 using the positioning stage 246. For example, a portion of the light emitted by the first light source 502 (e.g., the light of the first variable frequency $f_1$ or the visible alignment laser) may reflect off of the surface of the liquid sample 206 and be detected by the detector 506 or a second detector (not shown) of the SFG microscope 501. Alternatively, the detector 506 may detect the SFG signal. Based on a position or an intensity of the detected signal, the controller 232 controls the positioning stage 246 to align the liquid sample 206 with the convergence point of the spatially and temporally overlapped first and second light beams.

Figure 6A:
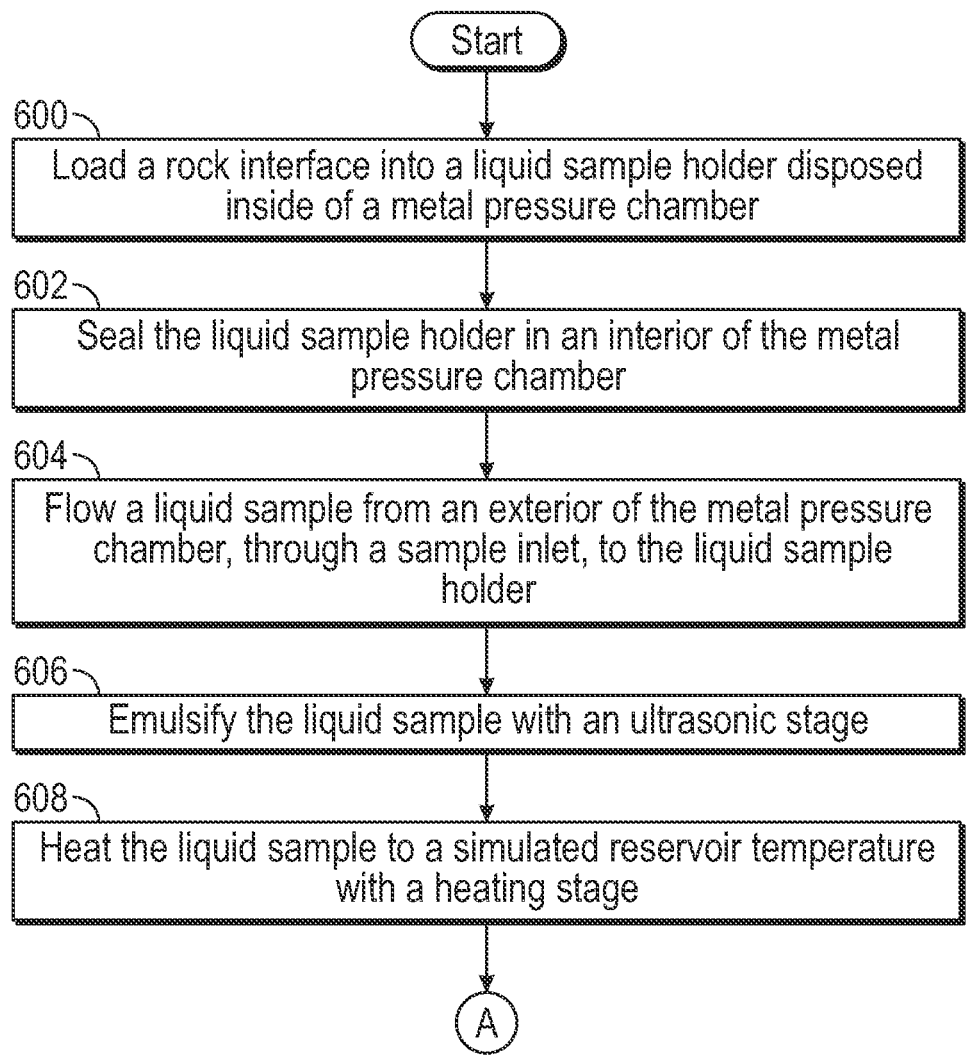
FIGS. 6A and 6B show a method for performing SFG spectroscopy according to one or more embodiments.
Figure 6B:
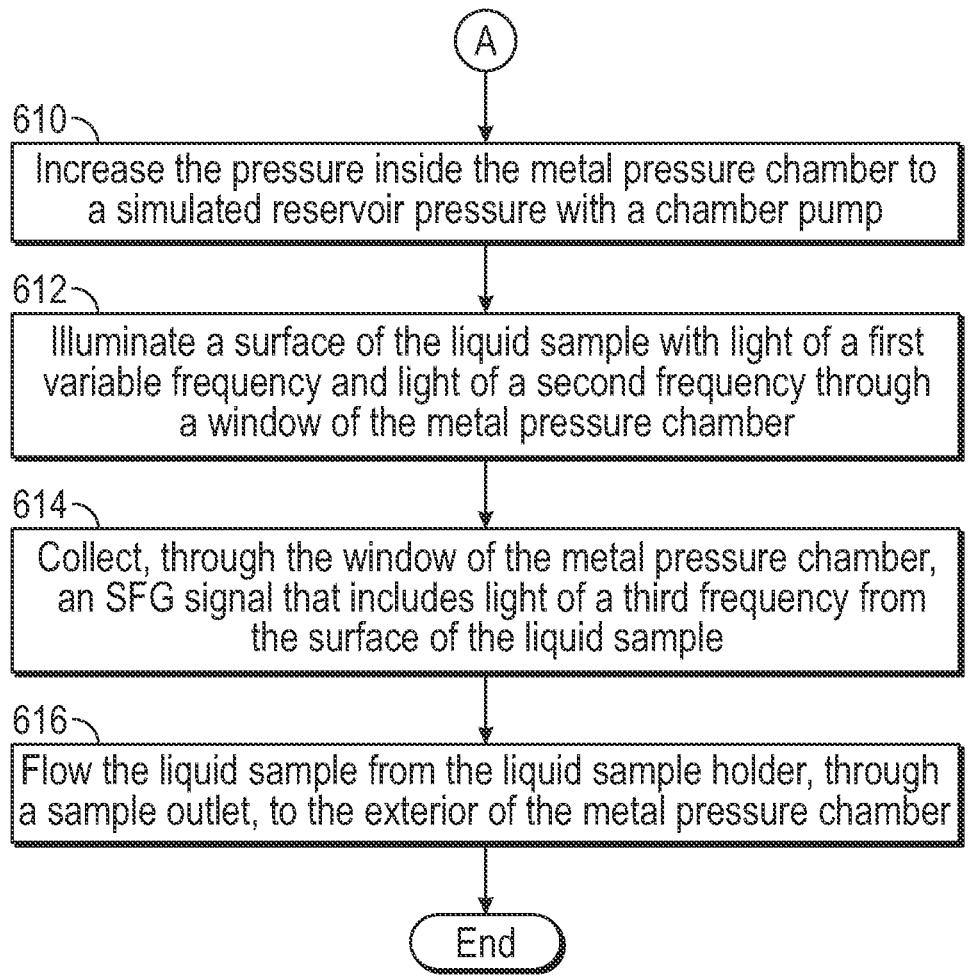

FIGS. 6A and 6B show a flowchart according to one or more embodiments. The flowchart depicts a method for performing SFG spectroscopy that may be performed using the pressure cell 200 described above in reference to FIGS. 2, 3, and 5. In one or more embodiments, one or more of the steps shown in FIGS. 6A and 6B may be combined, omitted, repeated, and/or performed in a different order than the order shown in FIGS. 6A and 6B. Accordingly, the scope of the present disclosure should not be considered limited to the specific arrangement of steps shown in FIGS. 6A and 6B.

At 600, a rock interface 207 is loaded into a liquid sample holder 204 disposed inside of a metal pressure chamber 202 that includes a base 208 and a removable lid 210. The rock interface 207 may be a calcite rock sample or any other appropriate material that may simulate liquid/solid interactions or liquid/solid interfaces that occurring in a reservoir 102 (FIG. 1).

At 602, the removable lid 210 is sealed onto the base 208 to seal the liquid sample holder 204 in an interior of the metal pressure chamber 202. The seal may be formed by screwing, clipping, mechanical fastening (e.g., with bolts, screws) the removable lid 210 onto the base 208. However, the removable lid 210 may be sealed to the base 208 by any appropriate means that provides a seal to contain the pressure of the simulated reservoir environment. In one or more embodiments, a seal 212 (e.g., elastomeric O-ring, copper gasket, or other seal) may be disposed between the base 208 and the removable lid 210 to seal the metal pressure chamber 202.

At 604, a liquid sample 206 is flowed from an exterior of the metal pressure chamber 202, through a sample inlet 216, to the liquid sample holder 204. In one or more embodiments, the liquid sample 206 may be a brine comprising a mixture of an aqueous phase and an organic phase that is flowed through a single sample inlet path 218. The flow of the liquid sample 206 in the sample inlet path 218 may be generated by a sample pump 220.

In another embodiment, the aqueous phase and organic phase of the liquid sample 206 may be separate liquids that are flowed into the liquid sample holder 204 by separate sample inlet paths 218a, 218b. The relative proportions of the aqueous and organic phases introduced into the liquid sample holder 204 may be controlled by separate sample pumps 220a, 220b that are connected to the corresponding sample inlet paths 218a, 218b.

At 606, an ultrasonic stage 228 emulsifies the liquid sample 206. In one or more embodiments including a mixture of an aqueous phase and an organic phase (e.g., a brine) as the liquid sample 206, the ultrasonic stage 228 may sonicate the liquid sample 206 to emulsify the two phases.

At 608, a heating stage 238 heats the liquid sample 206 to a simulated reservoir temperature. In one or more embodiments, the temperature of the liquid sample 206 is raised to approximately 90-100 C°. However, as discussed above, the present disclosure is not limited to this temperature range because conditions of a reservoir 102 may vary according to many parameters (e.g., depth, geographic location, rock composition). The temperature of the liquid sample 206 may be monitored by a thermocouple 244 that is connected to the liquid sample holder 204. The thermocouple 244 may send temperature information to a temperature controller 242, or alternatively a controller 232, that sends power and control signals to the heating stage 238.

At 610, a chamber pump 230 connected to the interior of the metal pressure chamber 202 increases the pressure inside the metal pressure chamber 202 to a simulated reservoir pressure. In one or more embodiments, the pressure of the liquid sample 206 is raised to approximately 3000 psi. However, as discussed above, the present disclosure is not limited to this approximate pressure value because conditions of a reservoir 102 may vary according to many parameters (e.g., depth, geographic location, rock composition). The pressure of the interior of the metal pressure chamber 202 may be monitored by a pressure gauge 234. The pressure gauge 234 may send pressure information to the controller 232 that sends power and control signals to the chamber pump 230. Furthermore, the controller 232 may control a control valve 236 to seal the metal pressure chamber 202 from the chamber pump 230 or release pressure from the interior of the metal pressure chamber 202.

At 612, a surface of the liquid sample 206 is illuminated with light of a first variable frequency $f_1$ and light of a second frequency $f_2$ through a window 214 of the metal pressure chamber 202. The incident light beams of the first and second frequencies $f_1$, $f_2$ are spatially and temporally overlapped at the surface of the liquid sample 206 to generate an SFG signal (i.e., light of the third frequency $f_3$ that is the sum of the first and second frequencies $f_1$, $f_2$).

In one or more embodiments, a positioning stage 246 may translate the surface of the liquid sample 206 to align the surface of the liquid sample 206 with the incident first and second light beams. The positioning stage 246 may automatically position the surface of the liquid sample 206 based on a reflected signal from the surface of the liquid sample 206 (e.g., alignment with the surface of the liquid sample 206 is achieved when the reflected signal exceeds a predetermined threshold or reaches a predetermined position on a detector 506). Alternatively, the positioning stage 246 may automatically position the surface of the liquid sample 206 based on an intensity of the generated SFG signal (e.g., alignment with the surface of the liquid sample 206 is achieved when the SFG signal is maximized or exceeds a predetermined threshold). In yet another embodiment, the positioning stage 246 may be controlled manually.

At 614, the SFG signal comprising light of a third frequency $f_3$ is collected from the surface of the liquid sample 206 for analysis.

At 616, the liquid sample 206 is flowed from the liquid sample holder 204, through a sample outlet 222, to the exterior of the metal pressure chamber 202. In one or more embodiments, the liquid sample 206 that is removed from the metal pressure chamber may be replace by a new liquid sample 206 from the sample inlet path 218.

In other words, in one or more embodiments, the composition of the liquid sample 206 may be altered in situ by flowing different solutions or different proportions of the aqueous phase and organic phase into the liquid sample holder 204 and removing the liquid sample 206 that has already been studied. Thus, the liquid sample 206 may be characterized in both static and dynamic reservoir compositions (e.g., stable live oil compositions or dynamically changing compositions that may model displacement of hydrocarbons by an injection fluid).

In one or more embodiments, In one or more embodiments, the heating stage 238 and the chamber pump 230 may dynamically change the temperature and pressure inside the metal pressure chamber 202 during acquisition of the SFG signal. For example, the controller 232 may ramp the temperature or pressure to different values in response to data collected from the pressure gauge 234, the control valve 236, the thermocouple 244, the detector 706, or any combination thereof. Thus, the liquid sample 206 may be characterized in both static and dynamic reservoir environments (e.g., stable temperature and pressure conditions or dynamically changing temperature and/or pressure conditions).

In one or more embodiments, the first variable frequency $f_1$ may be continuously or discretely changed to obtain a spectrum of SFG signals from the liquid sample 206. In another embodiment, first variable frequency $f_1$ may be a spectrally broadband frequency range that includes a plurality of frequencies. Accordingly, a spectrum of SFG signals from the liquid sample 206 may be obtain at one time.

Software instructions in the form of computer readable program code to perform embodiments of the present disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments disclosed herein.

One or more of the embodiments disclosed herein may have one or more of the following advantages and improvements over conventional SFG spectroscopy techniques: simulating reservoir conditions (e.g., high pressure, high temperature environments); simulating reservoir interactions for study in a controlled environment; SFG spectroscopy under static and dynamic temperature and/or pressure conditions; SFG spectroscopy with dynamic sample compositions to analyze more accurate liquid/liquid and liquid/solid interfaces that occur in hydrocarbon reservoirs. One or more of the above advantages may improve a user's understanding of the chemical and molecular structures and interfaces that occur in a reservoir and improve the effectiveness of hydrocarbon recovery techniques.

Although the disclosure has been described with respect to only a limited number of embodiments, those skilled in the art, having benefit of this disclosure, will appreciate that various other embodiments may be devised without departing from the scope of the present disclosure. Accordingly, the scope of the disclosure should be limited only by the attached claims.

What is claimed is:

1. A system for sum frequency generation spectroscopy, the system comprising:
    a pressure cell comprising:
        a metal pressure chamber including:
            a liquid sample holder that retains a liquid sample;
            a removable lid that seals against a base to enclose the liquid sample holder in an interior of the metal pressure chamber;
            a window in the removable lid that allows the liquid sample to be optically accessed from an exterior of the metal pressure chamber;
            a sample inlet that flows the liquid sample from the exterior of the metal pressure chamber to the liquid sample holder in the interior of the metal pressure chamber at a predetermined flow rate; and
            a sample outlet that flows the liquid sample from the liquid sample holder to the exterior of the metal pressure chamber;
        a heating stage, disposed in the interior of the metal pressure chamber, that heats the liquid sample;
        an ultrasonic stage, disposed in the interior of the metal pressure chamber, that emulsifies the liquid sample;
        a chamber pump, connected to the interior of the metal pressure chamber, that pressurizes the interior of the metal pressure chamber; and
        a controller that controls the chamber pump, the ultrasonic stage, and the heating stage to control a pressure of the interior of the metal pressure chamber, an emulsification of the liquid sample, and a temperature of the liquid sample, respectively; and
    a sum frequency generation microscope comprising:
        a first light source that generates light of a first variable frequency;
        a second light source that generates light of a second frequency; and
        a detector that detects light.

2. The system according to claim 1, wherein
    the sample inlet comprises:
        a sample inlet path connected to the liquid sample holder; and
        a sample pump that pumps the liquid sample through the sample inlet path and into the liquid sample holder, wherein
    the controller controls the predetermined flow rate of the sample pump.

3. The system according to claim 1, wherein
    the sample inlet comprises a plurality of sample inlet paths, and
    each of the plurality of sample inlet paths is connected to a corresponding sample pump that pumps a portion of the liquid sample into the liquid sample holder.

4. The system according to claim 3, wherein
    a first sample inlet path of the plurality of sample inlet paths flows an aqueous phase of the liquid sample into the liquid sample holder,
    a second sample inlet path of the plurality of sample inlet paths flows an organic phase of the liquid sample into the liquid sample holder, and
    the ultrasonic stage emulsifies the liquid sample to create a brine from the aqueous and organic phases.

5. The system according to claim 1, wherein the heating stage and the ultrasonic stage are directly connected to the liquid sample holder.

6. The system according to claim 5, further comprising a thermal insulation layer that thermally isolates the heating stage from the metal pressure chamber.

7. The system according to claim 1, wherein
    the pressure cell further comprises:
        a pressure gauge that measures the pressure of the interior of the metal pressure chamber;
        a control valve that seals the interior of the metal pressure chamber from the chamber pump;
        a thermocouple that measures the temperature of the liquid sample; and
        an inlet valve and an outlet valve that seal the sample inlet path and sample outlet path, respectively, wherein
    the controller controls the chamber pump, the control valve, the inlet valve, and the outlet valve based on the pressure measured by the pressure gauge, and
    the controller controls the heating stage based on the temperature measured by the thermocouple.

8. The system according to claim 1, wherein the liquid sample holder further comprises a rock interface that interacts with the liquid sample.

9. The system according to claim 1, further comprising a positioning stage that automatically positions a surface of the liquid sample based on optical feedback from the surface of the liquid sample.

10. A method of performing sum frequency generation spectroscopy in a pressure cell, the method comprising:
    sealing a liquid sample holder in an interior of a metal pressure chamber of the pressure cell, wherein the metal pressure chamber comprises a base and a removable lid;
    flowing a liquid sample from an exterior of the metal pressure chamber, thorough a sample inlet, to the liquid sample holder in the interior of the metal pressure chamber at a predetermined flow rate;
    emulsifying the liquid sample with an ultrasonic stage;
    heating the liquid sample with a heating stage;
    pressurizing the interior of the metal pressure chamber with a chamber pump that is connected to the interior of the metal pressure chamber;

illuminating a surface of the liquid sample with light of a first variable frequency and light of a second frequency through a window of the metal pressure chamber;

collecting, through the window, light of a third frequency from the surface of the liquid sample, wherein the third frequency is the sum of the first variable frequency and the second frequency; and flowing the liquid sample from the liquid sample holder, through a sample outlet, to the exterior of the metal pressure chamber.

11. The method according to claim 10, further comprising:

pumping the liquid sample through a sample inlet path with a sample pump, wherein the sample inlet path is connected to the liquid sample holder.

12. The method according to claim 10, further comprising:

pumping a plurality of portions of the liquid sample through a plurality of sample inlet paths of the sample inlet and into the liquid sample holder, wherein each sample inlet path of the plurality of sample inlet paths includes a corresponding sample pump.

13. The method according to claim 12, further comprising:

pumping an aqueous phase of the liquid sample into the liquid sample holder from a first sample inlet path of the plurality of sample inlet paths; and pumping an organic phase of the liquid sample into the liquid sample holder from a second inlet path of the plurality of sample inlet paths, wherein emulsifying the liquid sample with the ultrasonic stage creates a brine from the aqueous and organic phases.

14. The method according to claim 10, further comprising directly connecting the heating stage and the ultrasonic stage to the liquid sample holder.

15. The method according to claim 10, further comprising:

measuring a pressure of the interior of the metal pressure chamber with a pressure gauge; and measuring a temperature of the liquid sample with a thermocouple;

controlling the chamber pump, a control valve that seals the interior of the metal pressure chamber from the chamber pump, an inlet valve that seals the sample inlet path, and an outlet valve that seals the sample outlet path based on the pressure measured by the pressure gauge, and controlling the heating stage based on the temperature measured by the thermocouple.

16. The method according to claim 10, further comprising:

positioning the surface of the liquid sample to align the surface of the liquid sample with the light of the first variable frequency and the light of the second frequency.

17. The method according to claim 16, wherein the positioning comprises automatically positioning the surface of the liquid sample based on a reflected signal from the surface of the liquid sample.

18. The method according to claim 16, wherein the positioning comprises automatically positioning the surface of the liquid sample based on an intensity of a sum frequency generation signal.

* * * * *